United States Patent
Dreyer

(10) Patent No.: US 7,230,032 B2
(45) Date of Patent: *Jun. 12, 2007

(54) CALCIUM BLOCKERS TO TREAT PROLIFERATIVE VITREORETINOPATHY

(75) Inventor: Evan B. Dreyer, Pittsburgh, PA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/436,902

(22) Filed: May 12, 2003

(65) Prior Publication Data

US 2003/0199551 A1 Oct. 23, 2003

Related U.S. Application Data

(63) Continuation of application No. 10/038,215, filed on Jan. 2, 2002, now Pat. No. 6,573,280, which is a continuation of application No. 09/445,832, filed as application No. PCT/US98/12414 on Jun. 15, 1998, now Pat. No. 6,380,261.

(60) Provisional application No. 60/051,962, filed on Jun. 30, 1997.

(51) Int. Cl.
A61K 31/135 (2006.01)

(52) U.S. Cl. ...................... 514/656; 514/912

(58) Field of Classification Search ................ 514/317, 514/656, 912; 424/78.04
See application file for complete search history.

(56) References Cited

U.S. PATENT DOCUMENTS

| | | | |
|---|---|---|---|
| 4,755,388 A | 7/1988 | Heath et al. | |
| 5,424,321 A | 6/1995 | Hellberg et al. | |
| 5,431,907 A | 7/1995 | Abelson et al. | |
| 5,516,522 A | 5/1996 | Peyman et al. | |
| 5,527,810 A | 6/1996 | Ornstein | |
| 5,597,809 A | 1/1997 | Dreyer | |
| 5,602,156 A | 2/1997 | Kohn | |
| 5,623,051 A | 4/1997 | Caterall et al. | |
| 5,710,165 A | 1/1998 | Kapin et al. | |
| 6,509,355 B1 | 1/2003 | Collier, Jr. | |
| 6,573,280 B2 | 6/2003 | Dreyer | |

FOREIGN PATENT DOCUMENTS

| | | |
|---|---|---|
| WO | WO 90/06118 | 6/1990 |
| WO | WO 91/02497 | 3/1991 |
| WO | WO 94/13275 | 6/1994 |
| WO | WO 95/22979 | 8/1995 |

OTHER PUBLICATIONS

Machamer (1978) British J. Ophthal. 62:737.
Hilton et al (1983) Ophthalmology 90:121.
Constable I: "Biological and Therapeutic Aspects of Proliferative Vitreoretinopathy" Japanese Journal of Ophthalmology, vol. 31, No. 4, 1987, pp. 513-520, XP008054876.
Uchida N. et al: "Glutamate Stimulates Proliferation of Retinal Pigment Epithelium and Its BFGF Expression Through NMDA Receptor Activation", vol. 71, No. Suppl. 1, Mar. 20, 1996, p. 274P, XP008040806.
Murphy T L et al: "Migration of retinal pigment epithelium cells in vitro is regulated by protein kinase C", Experimental Eye Research, vol. 60, No. 6, Jun. 1995, pp. 683-695, XP-002102540.
Uchida N. et al: "Gltamate-Stimulated Proliferation of Rat Retinal Pigment Epithelium: Through NMDA Receptor Activation and BFGF Expression", Investigative Ophthalmology & Visual Science, vol. 37, No. 3, Apr. 21, 1996, pp. S388, XP008040803.
Sakamoto T et al: "Vitamin E Succinate Inhibits Proliferation and Migration of Retinal Pigment Epithelial Cells in Vitro-Therapeutic Implication for Proliferative Vitreoretinopathy", Graefe's Archive for Clinical and Experimental Ophthalmology, vol. 234, No. 3, Mar. 1996, XP008040829.
Hackett S. et al: Cyclic 3',5'-Adenosine Monophosphate Modulates Retinal Pigment Epithelial Cell Migration in Vitro, vol. 104, No. 11, Nov. 1986, pp. 1688-1692, XP008054877.
Hackett S. et al: "Implication of Protein Carboxymethylation in Retinal Pigment Epithelial Cell Chemotaxis", Ophthalmic Research, vol. 20, No. 1, 1988, pp. 54-59.
Wagner M. et al: "Effects of Pharmacological Modulation of Intracellular Signalling Systems on Retinal Pigment Epithelial Cell Attachment to Extracellular Matrix Protein", Current Eye Research, vol. 14, No. 5, May 1995, pp. 373-384.
Kalloniatis M.:"Amino Acids in Neurotransmission and Disease", Journal of the American Optometric Assoc., vol. 66, No. 12, Dec. 1995, pp. 750-757, XP008053708.
Solberg Y et al: "Treatment of Laser-Induced Retinal Injuries by Neuroprotection", SPIE, vol. 2974, 1997, pp. 158-165.
Ishikawa S. et al: "Alteration of Glutamine Concentration in the Vitreous Humor in Patients with Proliferative Vitreoretinopathy", Current Eye Research, vol. 14, No. 3, Mar. 1995, pp. 191-197, XP008053697.
Haberecht M. et al: "N-Methyl-D-Aspartate-Mediated Glutamate Toxicity in the Developing Rabbit Retina" Journal of Neuroscience Research, vol. 47, No. 4, Feb. 15, 1997, pp. 416-426, XP008040828.
Uchida et al: "Glutamate-Stimulated Proliferation of Rat Retinal Pigment Epithelial Cells", European Journal of Pharmacology, vol. 343, No. 2/3, Feb. 19, 1998, pp. 265-273, XP008040812.
Parsons, C.G., et al., *Comparison of the potency, kinetics and voltage-dependency of a series of uncompetitive NMDA receptor antagonists* in vitro *with anticonvulsive and motor impairment activity* in vivo, Neuropharmacology, Oct. 1995; 34(10): 1239-58.

(Continued)

Primary Examiner—Zohreh A. Fay
(74) Attorney, Agent, or Firm—Brent A. Johnson; Martin A. Voet

(57) ABSTRACT

Glutamate causes migration and proliferation of retinal pigment epithelium and/or glial cells, and glutamate antagonists can prevent, treat or reduce retinal pigment epithelium and/or glial migration and the subsequent development of proliferative vitreoretinopathy. Avoidance or management of proliferative vitreoretinopathy can be achieved by administering to the patient a compound capable of reducing glutamate-induced retinal cell migration in a concentration effective to reduce such migration.

1 Claim, No Drawings

OTHER PUBLICATIONS

Zajaczkowski, W., et al., *Behavioural evaluation of long-term neurotoxic effects of NMDA receptor antagonists*, Neurotox Res. Apr. 2000; 1(4):299-310.

Ehren, M., et al., *Inhibition of RPE proliferation, attachment and migration by carboxyamido-triazole (CAI), a drug which acts b modifying calcium mediated signal transduction*, Investigative Ophthalmology and Visual Science, vol. 38, No. 4 part 1-2 May 1997, p. S754.

Hahn, J.M., et al., *Calcium channel blocker mediated inhibition of retinal pigment epithelial cell contraction of a collagen gels*, Investigative Ophthalmology and Visual Science, vol. 37, No. 3, 1996, p. S393.

Hoffmann, S., et al., *Effect of the Calcium-antagonist verapamil on the serum induced proliferation of RPE cells* in vitro, Investigative Ophthalmology and Visual Science, vol. 37, No. 3, 1996, pp. S389.

Richter D., et al. *Growth inhibition of intraocular proliferative explants under* in vitro *conditions by verapamil*, Klinische Monatsblatter Fur Augenheilkunde, Sep. 1993, vol. 203, No. 3, pp. 206-211.

CALCIUM BLOCKERS TO TREAT PROLIFERATIVE VITREORETINOPATHY

CROSS REFERENCE TO RELATED PATENT APPLICATIONS

This patent application is a continuation of U.S. patent application Ser. No. 10/038,215, filed on Jan. 2, 2002 now U.S. Pat. No. 6,573,280, which is a continuation of U.S. patent application Ser. No. 09/445,832 which was filed on Dec. 13, 1999 now U.S. Pat. No. 6,380,261, as the U.S. National Patent Application of PCT/US98/12414, which was filed on Jun. 15, 1998 and was based on U.S. Provisional Application 60/051,962, which was filed on Jun. 30, 1997 in the name of Dreyer for CALCIUM BLOCKERS TO TREAT PROLIFERATIVE VITREORETINOPATHY.

BACKGROUND OF THE INVENTION

This application relates to preventing, controlling reducing and/or treating proliferative vitreoretinopathy. Proliferative vitreoretinopathy (including epiretinal membrane formation) is a potentially devastating ophthalmic condition that can lead to blindness. It can develop after any penetration of the eye—surgical or traumatic. Predisposing conditions therefore include, but are not limited to, penetrating trauma, retinal tears, traction detachments, vitrectomy, and intraocular surgery. Any ophthalmic condition that precipitates or permits migration of retinal pigment is epithelium or glial cells can lead to the development of proliferative vitreoretinopathy. See Machamer (1978) British J. Ophthal. 62:737; Hilton et al. (1983) Ophthalmology 90:121.

SUMMARY OF THE INVENTION

I have discovered that glutamate causes migration and proliferation of retinal pigment epithelium and/or glial cells. The invention features the use of glutamate antagonists to reduce or control retinal pigment epithelium and/or glial migration and the subsequent development of proliferative vitreoretinopathy. Avoidance or management of proliferative vitreoretinopathy can be achieved by administering to the patient a compound capable of reducing glutamate-induced retinal pigment epithelium and/or glial migration in a concentration effective to reduce such migration.

While I do not wish to be bound to any specific theory, I conclude that one or more of the several types of calcium-permeable CNS ion channels mentioned below can be involved in controlling such migration, including: a) the various aspects of the NMDA (N-methyl-D-aspartate) receptor channel complex; b) the voltage-dependent $Ca^{2+}$ channels; and c) other channels directly coupled to glutamate (or excitatory amino acid) receptors. Such channels are reviewed in: Sommer, B. and Seeburg, P. H. "Glutamate receptor channels: novel properties and new clones" *Trends Pharmacological Sciences* 13:291-296 (1992); Nakanishi, S., "Molecular Diversity of glutamate receptors and implications for brain function", *Science* 248: 597-603 (1992).

One aspect of the invention generally features a method of treating, preventing, or reducing proliferative vitreoretinopathy in a patient by administering to the patient's retina an effective amount of a compound that reduces CNS neuronal damage incident to (associated with) is calcium ion influx.

A second aspect of the invention features treating, preventing, or reducing proliferative vitreoretinopathy in a patient by administering to the patient's retina an effective amount of at least one of the compounds listed in one or more of Tables 2-5. below.

A third aspect of the invention features treating preventing or reducing proliferative vitreoretinopathy in a patient by administering to the patient's retina an effective amount of a compound that reduces glutamate related retinal cell migration, proliferation, or both.

The compound may be one of the so-called NMDA antagonists—i.e., it reduces neuronal damage mediated by the NMDA receptor complex. Alternatively, the compound antagonizes neuronal damage mediated by the voltage-dependent calcium channel. Other useful compounds are those which limit release of glutamate from cells or reduce the intracellular neurotoxic consequences of glutamate interaction with cell membrane glutamate receptors. Preferably, the compound crosses the blood-retinal barrier.

The patient may be anyone who has experienced, or is at risk for experiencing, penetrating trauma, retinal tear, traction detachment, vitrectomy, or intraocular surgery. The compound may be administered to the patient topically, orally, or intravitreally, as well as by other routes described below. It may be administered chronically, i.e., over an extended period of a month or even six months or years.

The invention preferably will be used to treat patients having proliferative vitreoretinopathy or to treat patients prophylactically to avoid that condition. Preferably, the agent is administered over an extended period (e.g., at least six-months and preferably at least one year). Those at risk for developing proliferative vitreoretinopathy include patients who have experienced penetrating trauma, retinal tears, traction detachments, vitrectomy, or intraocular surgery.

Particularly preferred compounds are antagonists of the NMDA receptor-channel complex. The term "NMDA receptor antagonists" includes several sub-types of NMDA antagonists including: a) channel blockers—i.e., antagonists that operate uncompetitively to block the NMDA receptor channel; b) receptor antagonists—antagonists that compete with NMDA to act at the NMDA binding site; c) agents acting at either the glycine co-agonist site or any of several modulation sites such as the zinc site, the magnesium site, the redox modulatory site, or the polyamine site; d) agents which inhibit the downstream effects of NMDA receptor stimulation, such as agents that inhibit activation of protein kinase C activation by NMDA stimulation, antioxidants, and agents that decrease phosphatidylinositol metabolism.

Other compounds that are useful in the invention include voltage-dependent calcium channel antagonists, e.g. those which exert a substantial direct effect on glutamate toxicity mediated by the L-type voltage dependent $Ca^{++}$ channel in that they produce a statistically significant result in experiments measuring glutamate induced effects by the general method described in Karschian and Lipton, *J. Physiol.* 418: 379-396 (1989) or by other techniques for measuring antagonism of the L-type $Ca^{++}$ channel known to those in the art. (We contrast the direct effect so measured with the secondary effects of excitoxicity mediated by other channels, which in turn causes flow through the voltage dependent $Ca^{++}$ channels.) Particular candidate compounds include Class I voltage dependent $Ca^{++}$ channel antagonists, e.g., phenylalkylamines.

Preferably, the compounds used cross the blood-retina barrier and can be administered chronically. Other useful agents act as antagonists of non-NMDA receptors (glutamate receptor types other than the NMDA receptor complex discussed above), and include agents which block inotropic glutamate receptors or interact with metabotropic glutamate receptors (Nakanishi, supra). Still other agents act to limit (reduce) release of glutamate from cells, thereby acting upstream from the glutamate receptors in the excitatory neurotoxicity process. Still other agents may act by blocking downstream effects of glutamate receptor stimulation, e.g., the intracellular consequences of glutamate interaction with a cell membrane glutamate receptor, such as agents (like dantrolene) that block the rise in intracellular calcium following stimulation of membrane glutamate receptors.

The most preferred compounds are those capable of crossing the blood-retinal barrier; these compounds may be administered orally, intravenously, or topically and cross intervening barriers including the blood-retina barrier to reach the retinal ganglion cells. Compounds that do not freely cross the blood-retina barrier are less preferred; these compounds may be administered intravitreally to the retina. In the case of compounds that have an intermediate ability to cross the blood-retina barrier, the mode of administration will depend on the dosage required and other factors.

Among the preferred compounds are amantadine derivatives (e.g., memantine, amantadine, and rimantadine), nitroglycerin, dextorphan, dextromethorphan, and CGS-19755. See generally, the compounds listed in Table 2.

The invention is useful for the reduction or prevention (including prophylactic treatment) of damage as a result of proliferative vitreoretinopathy Other features and advantages of the invention will be apparent from the following description of the preferred embodiments thereof, and from the claims.

DESCRIPTION OF THE PREFERRED EMBODIMENTS

Selection of Antagonists

In view of our discovery that glutamate is associated with proliferative vitreoretinopathy, the invention features antagonists having certain specific characteristics: the ability to cross the blood-retina barrier; and the ability to be administered chronically. Within those guidelines, any suitable antagonist of the glutamate induced excitotoxicity may be used in accordance with the invention. As mentioned, in preferred embodiments, N-methyl-D-aspartate (NMDA) subtype of glutamate receptor-channel complex may be used to reduce or prevent proliferative vitreoretinopathy-related injury. Many antagonists of the NMDA receptor have been identified (Watkins et al., *Trends in Pharmacological Sci.* 11:25, 1990, hereby incorporated by reference). There are several recognized sub-types of NMDA receptor including: a) channel blockers—i.e., antagonists that operate non-competitively to block the NMDA receptor channel; b) receptor antagonists—antagonists that compete with NMDA, acting at the NMDA binding site; c) agents acting at either the glycine co-agonist site or any of several modulation sites such as the zinc site, the magnesium site, the redox modulatory site, or the polyamine site; d) agents which inhibit the downstream effects of NMDA receptor stimulation such as agents that inhibit activation of protein kinase C activation by NMDA stimulation, antioxidants, and agents that decrease phosphatidylinositol metabolism.

Other compounds that are useful in this invention include non-NMDA receptor antagonists, such as agents is which block other types of inotropic glutamate receptors or interact with metabotropic glutamate receptors; voltage-dependent calcium channel antagonists (against L, N, T, and P type channels) (Bean, B. P. *Annu. Rev. Physiol.* 51:367-384 (1989); Hess, P. *Annu. Rev. Neurosci.* 13:337-356 (1990)), and are described in greater detail below; and agents which act to decrease the release of glutamate, thereby acting upstream in the excitatory neurotoxicity process.

Table 1, below, lists various suitable NMDA and non-NMDA receptors which do not operate via the voltage-dependent $Ca^{++}$ ion channel. Tables 2-4 list antagonists of the voltage dependent $Ca^{++}$ channel, which can be used by themselves in connection with the first aspect of the invention, and which can also be used in combination with other antagonists in the second aspect of the invention.

TABLE 1

| NMDA Antagonists | NMDA Antagonists | NMDA Antagonists |
|---|---|---|
| 1. Competitive NMDA Antagonists (act at agonist binding site) CGS-19755 (CIBA-GEIGY) and other piperidine derivatives, D-2-amino-5-phosphovalerate, D-2-amino-7-phosphonoheptanoate (AP7) | 2. Channel Blockers (Un-Competitive NMDA Antagonists) MK-801 (Dizocilpine) and other derivatives of dibenzyocycloheptene (Merck) | 3. Antagonists at Glycine Site of the NMDA Receptor Kynurenate, 7-chloro-kynurenate, 5,7-chloro-kynurenate, thio-derivatives, and other derivatives. (Merck) |
| CPP ([3-(2-carboxypiperazin-4-y-propyl-1-phosphonic acid]) | Sigma receptor ligands, e.g. Dextrorphan, dextromethorphan and morphinan derivatives (Hoffman La Roche) such as caramiphen and rimcazole (which also block calcium channels) | Indole-2-carboxylic acid |
| LY274614, CGP39551, CGP37849, LY233053, LY233536 | Ketamine, Tiletamine and other cyclohexanes | DNQX |
| O-phosphohomoserine | Phencyclidine (PCP) and derivatives, and pyrazine compounds | Quinoxaline or oxidiazole derivatives including CNQX, NBQX |
| MDL100,453 | Memantine, amantadine, rimantadine and derivatives CNS 1102 (and related bi- and tri-substituted guanidines) Diamines Conantokan peptide from *Conus geographus* Agatoxin-489 | Glycine partial agonist (e.g. Hoecht-Roussel P-9939) |

TABLE 1-continued

| NMDA Antagonists | NMDA Antagonists | NMDA Antagonists |
| --- | --- | --- |
| 4. Polyamine Site of NMDA Receptor | 5. Redox Site of NMDA Receptor | 6. Other Non-Competitive NMDA Antagonists |
| Arcaine and related biguanidines and biogenic polyamines | Oxidized and reduced glutathione | Hoechst 831917189 |
| Ifenprodil and related drugs Diethylenetriamine SL 82,0715 | PQQ (pyrroloquinoline quinone) Compounds that generate Nitric Oxide (NO) or other oxidation states of nitrogen monoxide (NO+, NO−) including those listed in the box below | SKB Carvedilol |
| 1,10-diaminodecane (and related inverse agonists) | Nitroglycerin and derivatives, Sodium Nitroprusside, and other NO generating listed on p. 5 of this table<br>Nitric oxide synthase (NOS) Inhibitors: Arginine analogs including N-mono-methyl-L-arginine (NMA); N-nitro-L-arginine (NNA); N-nitro-L-arginine methyl ester; N-iminoethyl-L-ornithine<br>Flavin Inhibitors: diphenyliodinium; Calmodulin inhibitors, trifluoperizine<br>Calcineurin Inhibitors, e.g., FK-506 (inhibits calcineurin and thus NOS diphosphoxylase) | |
| Inhibitors of Downstream Effects of NMDA | Inhibitors of Downstream Effects of NMDA | Non-NMDA Receptor Antagonists |
| 7. Agents to inhibit protein kinase C activation by NMDA stimulation (involved in NMDA toxicity)<br>MDL 27,266 (Merrill Dow) and triazole-one derivatives<br>Monosialogangliosides (eg GM1 of Fidia Corp.) and other ganglioside derivatives LIGA20, LIGA4 (may also effect calcium extrustion via calcium ATPase) | 8. Downstream effects from Receptor Activation<br><br>8a. To decrease phopshatidylinositol metabolism<br>kappa opioid receptor agonist: U50488 (Upjohn) and dynorphan<br><br>kappa opioid receptor agonist: PD117302, CI-977<br><br>8b. To decrease hydrogen peroxide and free radical injury, eg antioxidants<br>21-aminosteroid (lazoroids) such as U74500A, U75412E and U74005F U74389F, FLE26749, Trolox (water soluble alpha tocophenol), 3,5-dialkoxy-4-hydroxy-benzylamines<br>Compounds that generate Nitric Oxide (NO) or other oxidation states of nitrogen monoxide (NO+, NO−) including those listed in the box below<br>Nitroglycerin and derivatives, Sodium Nitroprusside, and other NO generating listed on p. 5 of this table<br>Nitric oxide synthase (NOS) inhibition: Arginine analogs including N-mono-methyl-L-arginine (NMA); N-amino-L-arginine (NAA); N-nitro-L-arginine methyl ester; N-iminoethyl-L-ornithine | 9A. Non-NMDA antagonists (Competitive)<br><br>CNQX, NBQX, YM900, DNQX, PD140532<br>AMOA (2-amino-3[3-9carboxymethoxyl-5-methoxylisoxazol-4-yl]propionate]<br><br>2-phosphophonoethyl phenylalanine derivatives, i.e. 5-ethyl, 5-methyl, 5-trifluoromethyl<br><br>9B. Non-NMDA Non competitive antagonists<br>GYK152466<br><br>Evans Blue |
| Agents Active at Metabotropic Glutamate Receptors | Decrease glutamate release | Drugs to decrease intracellular calcium following glutamate receptor stimulation |
| 10a. Blockers of Metabotropic Glutamate Receptors<br>AP3 (2-amino-3-phosphonoprionic acid)<br><br>10b. Agonists of Metabotropic Glutamate Receptors<br>(1S,3R)-1-Amino-cyclopentane-1,3-dicarboxylic acid [(1S,3R)-ACPD]. commonly ref as 'trans'-ACPD | 11. Agents to decrease glutamate release<br><br>Adenosine, and derivatives, e.g. cyclohexyladenosine<br>CNS1145<br><br>Conopeptides: SNX-111, SNX-183, SNX-230<br><br>Omega-Aga-IVA, toxin from venom of funnel web spider<br>Compounds that generate Nitric Oxide (NO) or other oxidation states of nitrogen monoxide (NO+, NO−) including those listed in the box below<br>Nitroglycerin and derivatives, Sodium | 12a. Agents to decrease intracellular cadium release<br>Dantrolene (sodium dantrium); Ryanodine (or ryanodine + caffeine)<br>12b. Agents inhibiting intracellular Calcium-ATPase<br>Thapsigargin, cyclopiazonic acid, BHQ ([2,5-di-(tert butyl)-1,4-benzohydroquinone; 2-5-di-(tert-butyl)-1,4benzohydroquinone]) |

TABLE 1-continued

| |
|---|
| Nitroprusside, and other NO generating listed on p. 5 of this table |
| Nitric oxide synthase (NOS) Inhibitors: Arginine analogs including N-mono-methyl-L-arginine (NMA); N-amino-L-arginine (NAA); N-nitro-L-arginine (NNA); N-nitro-L-arginine methyl ester; N-iminoethyl-L-ornithine |

| Additional NO-generating compound |
|---|
| Isosorbide dinitrate (isordil) |
| S-nitrosocaptopril (Snocap) |
| Serum albumin coupled to nitric oxide (SA-NO) |
| Cathepsin coupled to nitric oxide (cathepsin-NO) |
| Tissue plasminogen activator coupled to NO (TPA-NO) |
| SIN-1 (also known as SIN1 or molsidomine) |
| Ion-nitrosyl complexes (e.g., nitrosyl-iron complexes, with iron in the Fe2+ state) |
| Nicorandil |

TABLE 2

Antogonist of the Voltage Dependent Calcium Channels (N, L, T, P and other types)

dihydropyridines (e.g., nimodipine)
phenylalkylamines (e.g., verapamil, (S)-emopamil, D-600, D-888)
benzothiazepines (e.g., diltiazem and others)
bepridil and related drugs
diphenylbutylpiperdines
diphenylpiperazines (e.g., flunarizine/cinnarizine series)
HOE 166 and related drugs
fluspirilene and related drugs
toxins and natural compounds (e.g., snail toxins - ωconotoxin GVIA and GVIIA, maitotoxin, taicatoxin, tetrandine, helolena toxin, plectreurys toxin, funnel-web spider venom and its toxin fraction, agatoxins including ω-agatoxin IIIA and ω-agatoxin IVA.

TABLE 3

DIHYDROPYRIDINE CALCIUM CHANNEL ANTAGONISTS

| | |
|---|---|
| nifedipine | KW3049 |
| niludipine | oxodipine |
| PY108-068 (darodipine) | CD349 |
| mesudipine | TC81 |
| GX 1048 | YM-09730-5 or (4S)DHP |
| floridine | MDL72567 |
| nitrendipine | Ro18-3981 |
| nisoldipine | DHP-218 |
| nimodipine | nilvadipine |
| nicardipine | amlodipine |
| felodipine | 8363-S |
| PN200-110 (Isradipine) | iodipine |
| CV4093 | azidopine |

TABLE 4

OTHER CALCIUM CHANNEL ANTAGONISTS

| | |
|---|---|
| diclofurime | D-600 |
| pimozide | D-888 |
| prenylamine | Smith Kline 9512 |
| fendiline | ranolzine |
| perhexiline | lidoflazine |
| mioflazine | CERM-11956 |
| flunarizine/cinnarizine series | R-58735 |
| | R-56865 |
| verapamil | amiloride |
| dilfiazine | phenytoin |
| dipropervine | thioridazine |
| (S)-emopamil | tricyclic antidepressants |

In Vitro Assay

An antagonist may be tested for utility in the method of the invention by monitoring its effect on proliferative retinopathy as follows.

Cultured fibroblasts will be injected into the vitreous of the rabbit eye. After two weeks, the degree of vitreopathy can be assessed histologically. At the time of the initial insult, the animals will be treated with the compound under consideration.

Such models are well known. A few examples (hereby incorporated by reference) included Kiumura et al. *Human Gene Therapy*, 7:799-808 (1996); Sakamoto et al., *Ophthalmology* 102:1417-1421 (1995); Handa et al. *Experimental Eye Research* 62:689-696 (1996); Berger et al. 37: 2318-1325 (1996); de Souza et al. *Ophthalmologica* 209: 212-216 (1995); Nakagawa et al. *Ophthalmnology & Visual Science* 36:2388-2395 (1995); Steinhorst et al. *Archive for Clinical & Experimental Ophthalmology* 232:347-354 (1994).

Use

An effective receptor antagonist will cause a decrease in proliferative vitreoretinopathy. As described above, the preferred compounds which cross the blood-retinal barriers are preferably administered topically or orally in known, physiologically acceptable vehicles including tablets, liquid excipients and suspensions. Those skilled in the art will appreciate how to formulate acceptable therapeutics.

Antagonists may be compounded into a pharmaceutical preparation, using pharmaceutical compounds well-known in the art; the exact formulation and dosage of the antagonist compound depends upon the route of administration. Generally, the effective daily dose of the antagonists will range from 0.01 to 1000 mg/kg.

OTHER EMBODIMENTS

Other embodiments are within the following claims. In the method of the invention, a useful compound may be administered by any means that allows the compound access to the retina. The compounds useful in the method include antagonists of excitatory amino acid receptors (both NMDA and non-NMDA subtypes) that act to reduce retinal cell migration or proliferation or reduce binding of glutamate to the NMDA receptor. The antagonists can act at a modulatory site or a co-agonist site or by blocking the chain of events initiated by receptor activation.

Other embodiments are within the following claims.

What is claimed is:

1. A method for treating proliferative vitreoretinopathy comprising administering to a patient's retina having proliferative retinopathy an effective amount of memantine.

* * * * *

UNITED STATES PATENT AND TRADEMARK OFFICE
CERTIFICATE OF CORRECTION

PATENT NO. : 7,230,032 B2
APPLICATION NO. : 10/436902
DATED : June 12, 2007
INVENTOR(S) : Dreyer It is certified that error appears in the above-identified patent and that said Letters Patent is hereby corrected as shown below:

On the Title page, in field (56), under "Other Publications", in column 2, line 8, delete "Gltamate-Stimulated" and insert -- Glutamate-Stimulated --, therefor.

In column 1, line 65, after "(associated with)" delete "is".

In column 3, line 28, after "vitreoretinopathy" insert -- . --.

In column 4, line 24, after "as agents" delete "is".

In columns 5-6 (Table 1-continued), line 21, delete "diphosphoxylase" and insert -- diphosphorylase --, therefor.

In columns 5-6 (Table 1-continued), line 29, after "propionate" delete "]" and insert -- ) --, therefor.

In columns 5-6 (Table 1-continued), line 38, delete "(lazoroids)" and insert -- (lazaroids) --, therefor.

In columns 5-6 (Table 1-continued), line 50, delete "inhibition:" and insert -- inhibitors: --, therefor.

In columns 5-6 (Table 1-continued), line 53, after "L-arginine" insert -- (NNA): N-nitro-L-arginine --.

In columns 5-6 (Table 1-continued), line 66, delete "2-5-di-(tert-butyl)-1" and insert -- 2,5-di-(tert-butyl)-1 --, therefor.

In columns 7-8 (Table 1-continued), line 10, delete "compound" and insert -- compounds --, therefor.

In columns 7-8 (Table 1-continued), line 14, delete "(Snocap)" and insert -- (SnoCap) --, therefor.

In column 7, line 32, delete "Antogonist" and insert -- Antagonists --, therefor.

In column 7, line 33, after "types" insert -- ) --.

In column 7, line 39, delete "diphenylbutylpiperdines" and insert -- diphenylbutylpiperidines --, therefor.

UNITED STATES PATENT AND TRADEMARK OFFICE
CERTIFICATE OF CORRECTION

PATENT NO. : 7,230,032 B2
APPLICATION NO. : 10/436902
DATED : June 12, 2007
INVENTOR(S) : Dreyer It is certified that error appears in the above-identified patent and that said Letters Patent is hereby corrected as shown below:

In column 7, line 46, delete "helolena" and insert -- hololena --, therefor.

In column 8, line 59, delete "Ophthalmnology" and insert -- Ophthalmology --, therefor.

Signed and Sealed this

Twenty-first Day of August, 2007

JON W. DUDAS
*Director of the United States Patent and Trademark Office*